United States Patent [19]

Daub

[11] Patent Number: 5,027,463
[45] Date of Patent: Jul. 2, 1991

[54] TOOTHBRUSH

[76] Inventor: Craig C. Daub, 5222 E. Bald Eagle Blvd., White Bear Lake, Minn. 55110

[21] Appl. No.: 520,053

[22] Filed: May 7, 1990

[51] Int. Cl.$^5$ .......................... A46B 9/04; A46B 13/02
[52] U.S. Cl. .................................. 15/22.1; 15/167.1; 15/167.2; 300/21
[58] Field of Search .................... 15/22.1, 22.2, 167.1, 15/167.2; 300/21

[56] References Cited

U.S. PATENT DOCUMENTS

| 3,100,309 | 8/1963 | Gambino | 15/167.1 |
| 4,366,592 | 1/1983 | Bromboz | 15/22.1 |
| 4,493,125 | 1/1985 | Collis | 15/167.2 |

FOREIGN PATENT DOCUMENTS 2449513 4/1976 Fed. Rep. of Germany ..... 15/167.2

*Primary Examiner*—Edward L. Roberts

[57] ABSTRACT

A toothbrush for use in simultaneously brushing and cleaning the occlusal, lingual and buccal surfaces of the upper and lower teeth of a user. The toothbrush, in the preferred embodiment, is power-driven and includes bristle support member which anchors bristles from opposite surfaces thereof. The bristles are arranged in longitudinal rows including central rows, intermediate rows and outer rows. The central rows are straight while the intermediate and outer rows are curved for engaging the lingual and buccal surfaces. The bristles are shaped and arranged in a heating chamber while being anchored to the bristle support member.

5 Claims, 1 Drawing Sheet

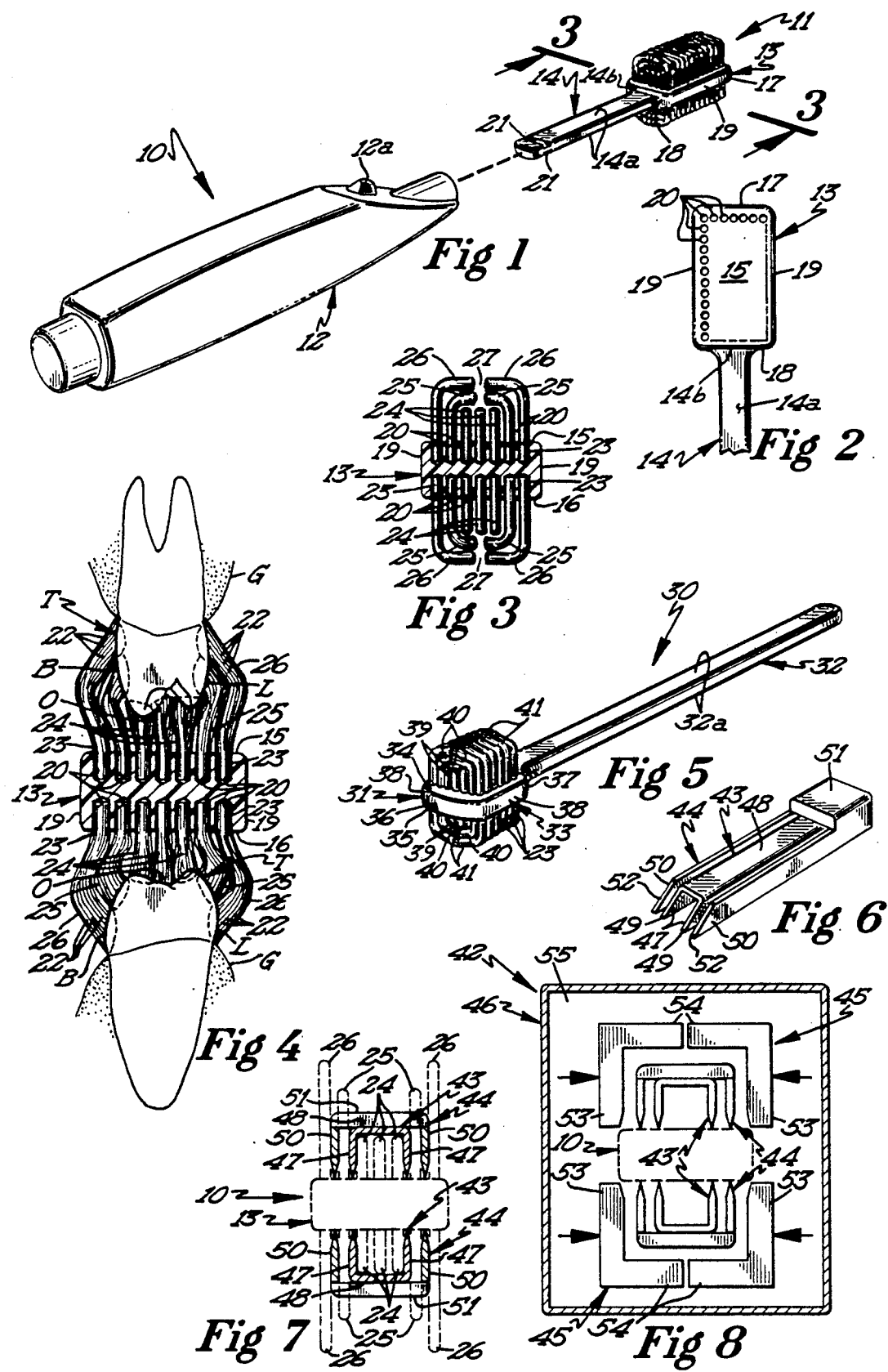

ion have
TOOTHBRUSH

FIELD OF THE INVENTION

This invention relates to toothbrushes and, more particularly, to a toothbrush which is completely effective in simultaneously brushing the upper and lower teeth plaque free.

BACKGROUND OF THE INVENTION

Research data indicates that the average person spends less than one minute brushing his or her teeth per day. On the other hand, dentists recommend that approximately three minutes of brushing three times per day is needed in order to maintain good oral hygiene. Apparently recognizing that the average person simply does not devote sufficient time in brushing his or her teeth, various designs in toothbrush construction have been developed to increase the cleaning efficiency for the individual but with limited success due to the human element involved.

Recommended brushing techniques have changed over the years. The fifties had the individual brushing up and down. Late sixties and seventies advocated the Bass technique of a circular motion. The mid eighties to present are now advocating a back and forth motion (reciprocating) to sweep the bristles below the gumline and break up the plaque. This reciprocating motion definitely has proved the most effective in the battle against periodontal disease and is supported by this toothbrush's reciprocating design.

It has been the endeavor to have all the qualities incorporated into this toothbrush. These qualities are a brush that is simple and easy to use, clinically effective with dramatic and immediate results, total plaque control, acceptable time expense, patient self-education, enjoyable and feels good, visual feedback, and sensory feedback from very smooth and clean teeth.

However, the human elements of handicaps, laziness, lack of knowledge in what is to be accomplished, lack of dexterity, amount of time spent brushing, and knowledge of proper and complete brushing skills has eluded both the user and the toothbrush industry. This is why 3 out of 4 adults have some form of periodontal disease (some experts say it is over 90%). Brushing alone is not enough, rather the complete removal of plaque is essential in the preservation of healthy teeth, gums, and supporting bone. Plaque is a soft, sticky, colorless film of bacteria constantly forming on our teeth. It combines with sugar and other carbohydrates to form acids, which attack tooth enamel and can cause cavities. Plaque can also cause inflammation of the gums (gingivitis), which can be identified by swollen, bleeding gums. If not treated early, gingivitis can lead to periodontitis, a more serious condition that causes gums to recede and bone to deteriorate. As a result, the supporting structures are weakened and teeth become loose. It is easy to see why thorough brushing to remove plaque is essential to keep teeth, gums, and bone healthy. We all know the importance of having the individuals remove plaque on a daily basis. We also recognize the difficulties associated with motivating them to comply with a consistent and conscientious home dental care regimen. The public needs a regimen that is easy to adopt and easy to follow.

U.S. Pat. No. 3,100,309 to Gambino discloses a toothbrush which has rows of curved bristles and a straight row of bristles. The rows of bristles extend transversely of the handle and presents a rather cumbersome arrangement.

U.S. Pat. No. 4,382,309, to Collis, discloses a toothbrush having two outer rows of curved bristle tufts and a single row of short, straight bristle tufts which are intended to simultaneously brush the lingual, buccal, and occlusal surfaces of the teeth.

The general design in the Collis Patent probably would increase the cleaning efficiency of the toothbrush compared to the conventional toothbrush head. However, the use of a single central row of bristle tufts for brushing the occlusal surfaces and the single outer rows of bristle tufts for brushing the lingual and buccal surfaces in the Collis toothbrush is ineffective in achieving good oral hygiene, especially if the user brushes for less than one minute.

SUMMARY OF THE INVENTION

It is an object of this invention to provide a novel toothbrush which is completely effective during use to simultaneously brush the upper and lower teeth of the user plaque free.

More specifically, it is an object of this invention to provide a novel toothbrush for simultaneously brushing the buccal, lingual, and occlusal surfaces of the teeth for both the upper and lower arches. Because of its unique construction, a user of this novel toothbrush can achieve the equivalence of nine minutes of manual brushing in 1½ minutes not taking into account the speed at which the electric reciprocating brush head runs at.

The average individual has the capability of generating manually between 160–200 brushing strokes per minute. This novel toothbrush will reciprocate brushing strokes between 800–1700 RPM's depending on the force with which the user closes down on the toothbrush. This represents anywhere from a 700% to 1000% increase in the number of brushing strokes delivered per minute when compared with manual brushing.

In the preferred embodiment, my novel toothbrush comprises an electric brush to facilitate brushing by a user. However, a manual version of the novel toothbrush is substantially identical to the electrical embodiment, but preferably has fewer rows of bristles. The toothbrush includes a flat bristle support member having opposed flat surfaces provided with openings therein for accommodating bundles of tufted bristles. The bundles of tufted bristles are arranged in longitudinally extending rows.

The longitudinally aligned tufted bristle bundles include a plurality of interior or central rows which brush the occlusal surfaces of the teeth. A pair of intermediate rows is positioned outwardly of the outermost interior rows, and a pair of exterior rows is positioned outwardly of the intermediate rows. The interior rows of bristle bundles are straight, while the intermediate and exterior rows of bristle bundles are bent or curved and serve to brush the lingual and buccal surfaces of the teeth. The bristle tufts flex open to accommodate the wider molars and flex back in to clean the narrow anterior teeth. Because the brush head provides equal amounts of brushing to both arches as well as the occlusal, buccal, and lingual surfaces, there are no skipped areas due to human error. All of the rows of bristles are disposed in substantially parallel relation to the longitudinal edges of a bristle support member.

In the preferred embodiment, the bristles are preferably formed of polyester resin, (although any synthetic resin could theoretically be used) and the bristles are of uniform diameter. Since the flexibility (softness) and rigidity (stiffness) of the bristles of uniform diameter is a function of the bristle length, the exterior rows of bristles bundles, which are the longest, are the most flexible (softest). The intermediate rows of bristle bundles are shorter than the bristles of the exterior rows and are, therefore, less flexible and more rigid than the longer bristles of the exterior rows. The shorter bristles of the three interior rows are the most rigid of the bristles and brush the occlusal surfaces of the teeth. Since the exterior rows of tufted bristle bundles brush the lingual and buccal surfaces of the teeth between the mid-portion and gum line thereof, and since these exterior rows of bristles are the most flexible (softest), there is little likelihood that these bristles will damage or irritate healthy gums and or cervical (root) portion of the teeth. This design will allow the brush head to hold up longer with its various stiffnesses of bristles under occlusal load while breaking up the constantly forming plaque and stimulating gingival tissues back to heath.

In the method of shaping the bent bristles of the intermediate and exterior rows, dry heat (rather than steam heat) is used to soften the bristles. The tufted bristle bundles of the intermediate rows have their outer ends bent inwardly over the interior rows, while the bristles of the exterior rows are bent over the bristles of the intermediate rows. A uniquely constructed shaping device is employed, which exerts an inward bending force on the tufted bristle bundles without exerting a longitudinal force on these bristles. The shaping device applied to the tufted bristle bundles of the toothbrush head is placed in a heating chamber and heated to a temperature within the range of 350 to 380 degrees Fahrenheit for a period of approximately 10 minutes.

FIGURES OF THE DRAWINGS

FIG. 1 is an exploded perspective view of the preferred embodiment of the invention;

FIG. 2 is a plan view of a portion of the toothbrush illustrating certain detailed construction thereof;

FIG. 3 is a cross-sectional view taken approximately along the line 3—3 of FIG. 1 and looking in the direction of the arrows;

FIG. 4 is a cross-sectional view similar to FIG. 3 and illustrating the manner in which the various rows of bristles engage the occlusal, buccal, and lingual surfaces of the teeth of the upper and lower arches;

FIG. 5 is a perspective view of a manual embodiment of the toothbrush;

FIG. 6 is a perspective view of a component of the shaping device used to shape certain rows of bristles;

FIG. 7 is a cross-sectional view of certain components of the shaping device with the rows of bristles illustrated by dotted line configuration; and FIG. 8 is a cross-sectional view of the assembled shaping device as it appears during the shaping operation.

DESCRIPTION OF THE PREFERRED EMBODIMENT

Referring now to the drawings and, more specifically, to FIGS. 1-4, it will be seen that one embodiment of my novel toothbrush, designated generally by the reference numeral 10, is thereshown.

The toothbrush 10 includes a head 11 and a combination electric motor module and handle 12 detachably connected to the head. The head 11 is comprised of a generally rectangular-shaped flat bristle support member 13 having an interconnecting member 14 integrally formed therewith and projecting therefrom. The bristle support member 13 has a planar upper surface 15, a planar lower surface 16, a front edge 17, a rear edge 18 and opposed parallel longitudinal edges 19. The upper and lower surfaces each have a plurality of openings 20 therein.

In the embodiment shown, it will be seen that the openings 20 in each of the upper and lower surfaces are arranged in longitudinal rows extending from adjacent the front edge 17 of the bristle support member to a point adjacent the rear edge 18 thereof. It will also be noted that the upper and lower surfaces 14a of the interconnecting member 14 are offset as at 14b with respect to the plane defined by the upper or lower surfaces 15 and 16 of the bristle support member 13. It will further be noted that the free end portion of the interconnecting member 14 has a pair of coupling notches 21 therein for coupling connection in a well-known manner to the drive connection of the combination electric motor module and handle 12.

Each of the upper and lower surfaces of the bristle support member have a plurality of bristles 22 arranged in tufted bundles 23, which project into the openings 20 of the planar surface. In the embodiment shown, the bristles 22, which comprise each tufted bundle 23, are of the same diameter and are formed of polyester resin. Each has a diameter of approximately 0.006–0.007 inches. Many, if not most, commercial toothbrushes have bristles formed of nylon. The water absorption rate of nylon is many orders greater than the water absorption rate of polyester bristles. Therefore, the bristles used in Applicant's toothbrush will not even be noticeably affected (softness) by water absorption, even though the toothbrush is used over and over again and is continuously wetted during the brushing operation.

It will also be noted that the tufted bundles 23 of bristles are arranged in longitudinally extending rows on the upper and lower surfaces of the bristle support member 13. Each surface has three interior rows 24, the centermost of which extends down the longitudinal center line of the bristle support member 13. Each upper and lower surface also has a pair of intermediate rows 25, each being positioned outwardly of the outermost of the interior rows. Each upper and lower surface also has a pair of outer rows 26, each outer row 26 being located between a longitudinal edge 19 of the bristle support member and an intermediate row 25 of the tufted bundles. The bristles of the tufted bristle bundles extending substantially normal or perpendicularly from the planar surfaces of the bristle support member 13 as best seen in FIG. 3. It will be noted that the intermediate and exterior rows of bristle bundles have their outermost end portions bent approximately at an angle relative to their inner end portions. The bristles of one intermediate row and one exterior row are bent towards the bristles of the other intermediate row and other exterior row. It will also be noted that there is a longitudinal opening 27 between the ends of the opposed intermediate rows and the opposed exterior rows on each surface of the bristle support member.

In the embodiment shown, the bristles of the intermediate and exterior rows are bent inwardly at approximately 45 degrees, with respect to the vertical portions of the bristles.

In the embodiment shown, the bristles forming the tufted bundles 23 of the interior rows extend approximately 5 millimeters from the upper surface 15 or lower surface 16 of the bristle support member to the outer end of the bristle. The bristles forming the tufted bundles 23 of the intermediate rows, before bending, extend approximately 11 millimeters from the upper surface 15 or lower surface 16 of the bristle support member to the outer ends of the bristles. The bristles comprising the tufted bundles of the exterior rows 26, before bending, extend approximately 15 millimeters from the upper surface 15 or lower surface 16 of the bristle support member to the outer end of the bristles.

Referring now to FIG. 4, it will be seen that the shorter and rigid bristles comprising the tufted bundles of the interior rows 24 engage and clean the occlusal surfaces O of the teeth of the lower and upper arches. It will also be seen that the bristles comprising the tufted bundles of the intermediate rows 25 are of medium stiffness or rigidity and engage and clean the buccal surface B and lingual surface L of the teeth T from the occlusal surface O to mid-points thereof. The bristles comprising the tufted bundles of the exterior rows 26 are of the greatest softness or flexibility and clean the buccal (facial) surface B and lingual surface L from the mid-point of these teeth T to the gum G, as best seen in FIG. 4. The exterior bristles are of sufficient rigidity to effectively clean the buccal surface B and lingual surface L of the teeth, but are soft enough to prevent abrasion of the gums G.

Referring now to FIG. 5, it will be seen that a different embodiment of the toothbrush, designated generally by the reference numeral 30, is thereshown. The embodiment of the toothbrush illustrated in FIG. 5 is a manual toothbrush, and includes a head 31 and an elongate handle 32. The head and handle are made of a suitable rigid plastic material, and the handle 32 has upper and lower planar surfaces 32a. The head 31 of the toothbrush is substantially identical to that illustrated in the embodiment of FIGS. 1-4, with the exception that there are fewer bristle bundles in each of the rows of bristles projecting from the upper and lower planar surfaces of the bristle support member 33.

In this regard, the bristle support member 33 is of generally flat rectangular configuration, having a flat upper surface 34, a flat planar lower surface 35, a front edge 36, a rear edge 37, and longitudinal edges 38. The upper and lower surfaces of the bristle support member are provided with a plurality of openings therein in the manner of the embodiment of FIG. 1, and these openings are arranged in longitudinally extending rows. The respective upper and lower surfaces 32a of the handle 32 are offset downwardly from the respective upper and lower surfaces 35 and 36 of the bristle support member in the manner of the embodiment of FIG. 4.

The head 31 is provided with a plurality of bristles, and the bristles are bundled or grouped together to form a plurality of tufted bundles. These bundles are inserted into the openings in the upper and lower surfaces of the bristle support member 33 in the manner of the embodiment of FIGS. 1-4. The bundles of bristles projecting from each planar surface of the head 34 are arranged in longitudinally extending rows, including three interior rows 39, a pair of intermediate rows 40, each intermediate row positioned exteriorly of one of the outermost interior row, and a pair of exterior rows 41.

The arrangement and configuration of the bristle bundles comprising the rows is identical to that of the embodiment of FIG. 1, but it is pointed out that the toothbrush of FIG. 5 has only six bundles of bristles per row, while the embodiment of FIG. 1 has 12 bundles of bristles per row. By reducing the numbers of bristle bundles, a user of the manual toothbrush of FIG. 5 will encounter less frictional resistance during the brushing operation, and will be able to comfortably and effectively clean the occlusal, buccal, and lingual surfaces of the teeth of both the upper and lower arches.

Referring now to FIGS. 6, 7, and 8, it will be seen that a novel shaping device, designated generally by the reference numeral 42, is thereshown, and is used in Applicant's novel method of shaping the bristles of the intermediate and exterior rows of the toothbrush. The shaping device 42 includes an interior shaping member 43 and, an intermediate shaping member 44. The shaping device also includes a pair of exterior shaping members 45, which are used to shape the bristle bundles of the intermediate and exterior rows projecting from one surface of the bristle support member. Thus, two sets of these shaping members will be employed for simultaneously shaping the intermediate and exterior rows of the toothbrush. These shaping components are placed in a heating chamber structure 46 during the shaping operation, as best seen in FIG. 8.

Referring now to FIG. 6, it will be seen that the interior shaping member 43 is of inverted channel shaped configuration, and is provided with a pair of legs 47 disposed in substantially parallel relation with respect to each other and rigidly interconnected by a web 48. It will also be noted, as seen in FIG. 6, that the leading or front edges of the legs 47 are beveled or slanted, as at 49. The intermediate shaping member 44 is comprised of a pair of elongate substantially flat legs 50 which are disposed in substantially parallel relation with respect to each other, and which are rigidly interconnected at their rearmost end portions by a bridge element 51 integral with the upper edges of these legs.

The interior shaping member 43 is positioned interiorly of the intermediate shaping member 44 so that the legs 47 are spaced inwardly of, but are substantially parallel to, the legs 50. The vertical dimension of the legs 50 is slightly greater than the vertical dimension of the legs 48. In the embodiment shown, the interior shaping member 43 is physically separate from the intermediate shaping member, but it is pointed out that these shaping members could be rigidly interconnected at their rearmost end portions.

Each exterior shaping members 45 is of L-shaped configuration, including a vertical leg 53 and a horizontal leg 54. Referring now to FIG. 8, it will be seen that each exterior shaping member 45 is arranged with a corresponding mate so that the ends of the respective horizontal legs 54 are disposed in closely adjacent, but spaced apart, relation.

During the shaping operation, the interior shaping member will be positioned so that the legs 47 are disposed exteriorly of the outermost of the interior rows projecting from one surface of the bristle support member. The intermediate shaping member 44 will be positioned so that each leg 50 is disposed between an intermediate row and an exterior row. One of the novel features of this shaping device is the beveled front ends of the legs of the interior and intermediate shaping members. This allows an interior shaping member and an intermediate shaping member to be inserted and slid longitudinally as a unit along a planar surface of the bristle support member without distorting the individual bristles of each bundle. The downwardly beveled front ends of the legs 47, 50 of these shaping members diminishes the likelihood of pulling individual bristles in the direction of movement of the shaping members. Each tufted bundles spreads outwardly from associated opening in the bristle support member. By beveling the ends of the legs 47, 50, the leading ends of these beveled surfaces are located adjacent the planar surface of the bristle support member, and thereby diminishes the likelihood of producing a dragging effect on the bristles.

After the interior and intermediate shaping members are applied to the toothbrush against both the upper and lower surfaces thereof, as shown in FIG. 7, the pairs of exterior shaping members are then applied to the bristles in the manner of FIG. 8. With this arrangement, the bristles comprising the bundles of the exterior row are bent over the bristles comprising the bundles of the intermediate rows. The bristles of the intermediate and exterior rows on one surface of the bristle support member located adjacent one longitudinal edge thereof are bent towards the bristles on said one surface comprising the exterior and intermediate rows adjacent the other longitudinal edge.

The toothbrush with the various shaping members applied thereto is then placed in the heating chamber 55 of the heating chamber structure 46, and the bristles are heated to a temperature within the range of 350° to 380° Fahrenheit, preferably about 365° Fahrenheit for a period of 10 minutes.

It will be seen that the horizontal leg 54 of each exterior shaping member 45 will compress the outer end portions of the bristles comprising the intermediate and exterior rows inwardly and downwardly, while the web portion 48 of the interior shaping member will protect the interior rows of bristle bundles, while serving as a clamping surface against which bristles of the intermediate and exterior rows are urged.

The outer end portions of the bristles comprising the bundles for the intermediate and exterior rows will be bent at substantially right angles during the shaping operation. However, after the toothbrush is removed from the shaping device and is allowed to cool, the bristles will have some flexback memory and will flex back from the right angular position. The memory flexback effect is such that, even when the exterior rows of bristles are applied to the teeth during the brushing operation, these bristles of the exterior rows reach the gums G of the user.

After the bending operation, the outer end portions of the bristles of one intermediate row will engage the outer end portions of the bristles comprising the other intermediate row. Similarly, the outer ends of the bristles comprising the bundles of one exterior row will engage the outer ends of the bristles comprising the other exterior row. In order to provide the proper spacing between the outer ends of opposed rows of intermediate and exterior rows projecting from one planar surface of the bristle support member, the outer ends are cut to define the opening 27, as best seen in FIG. 3. Each opening 27 has a width dimension of a magnitude to accommodate a viscous toothpaste therein so that the tooth-paste may be applied during the brushing operation by the interior, intermediate, and exterior rows of bristles.

During the brushing operation, toothpaste will be applied to the bristles projecting from both planar surfaces of the bristle support member and into the respective openings 27.

The user will insert the brush into his mouth and bite against the bristles so that the teeth penetrate through the openings 27 and engage the upper ends of the bristles comprising the interior rows on both surfaces of the bristle support member. The actuator button 12a for the combination electric motor module and handle 12 will be advanced, which produces a longitudinal reciprocating action to the interconnecting member and the bristle support member. This reciprocating motion effectively brushes the user's teeth in a manner not heretofore possible with commercial and prior art tooth brushes.

The switch 12a is a variable speed switch which includes two nichrome wires and a wiper blade. When the switch is moved from the off position the motor is energized. The speed of the motor is increased as the switch 12a is further shifted in the "on" direction. Therefore the speed of the brush may be selectively determined by a user.

The reciprocating motion imparted through the bristles will simultaneously clean the buccal, lingual, and occlusal surfaces of opposing arches so that the user may obtain the equivalent of a 9-minute brushing in 1.5 minutes. It has been found that since a user bites against the upper and lower interior rows of bristles of the toothbrush during the brushing operation, the toothbrush is more balanced and minimizes the likelihood of a user experiencing a gag reflex. The three interior rows are necessary to cover the width of bicuspids and molars in order to effectively clean the pit/fissure configuration of these teeth. The intermediate and exterior rows on each longitudinal surface of the bristle support member fan out, as best seen in FIG. 4, to give a greater brushing surface, which is simply not found in prior art or available commercial toothbrushes.

My novel toothbrush is also effective in allowing people with handicaps to still be able to do a complete and thorough job of brushing without assistance. In this regard, the toothbrush illustrated in the embodiments of FIGS. 1–4 can be mounted in a suitable mounting device so that a person with a handicap (such as a broken arm), a person suffering from arthritis, a mentally retarded person, a person lacking dexterity, a paraplegic, or a person lacking knowledge in proper brushing. Further, the use of the novel toothbrush allows equal amounts of brushing time for both arches.

Thus, it will be seen that I have provided a toothbrush, which is not only novel and unique, but one which functions in a more efficient manner than any heretofore known comparable toothbrush.

What is claimed is:

1. A toothbrush comprising means defining an elogate handle,

A substantially flat elongate bristle support member having opposed planar surfaces and having substantially parallel longitudinal edges, A plurality of elongate bristles arranged in tufted bristle bundles secured to said opposed surfaces and extending outwardly therefrom, said tufted bristle bundles being arranged in parallel, spaced apart longitudinally extending rows on each surface and disposed substantiailly parallel to the said longitudinal edges, said rows on each surface of said bristle support member including plurality of interior rows, a pair of intermediate rows, each being disposed outwardly of separate ones of the outermost of the interior rows, and a pair of exterior rows, each being positioned outwardly of separate ones of said intermediate rows, the bristles comprising the intermediate rows having a length dimension greater than the length dimension of the bristles comprising the interior rows, and having a length dimension less than the length dimension of the bristles comprising the exterior rows, the outer portion of the bristles comprising one intermediate row and one exterior row being angularly bent towards the angularly bent outer portions of the other intermediate row and other exterior row whereby a user can simontaneously brush the occlusal, lingual and buccal surfaces of both the upper arch and lower arch of the user's teeth.

2. The invention as defined in claim 1 and a uniform longitudinally extending opening between the ends of the bristles of one intermediate row and one exterior row and the ends of the bristles of the other intermediate row and other exterior row.

3. The toothbrush as defined in claim 1 wherein said means defining said handle includes an electric motor and handle module, said bristle support member having an elongate interconnecting member integral therewith and extending longitudinally therefrom and being connected with said electric motor and handle module whereby when the latter is energized, said bristle support member will be longitudinally reciprocated.

4. The toothbrush as defined in claim 1 wherein each of said planar surfaces has three interior rows of bristle bundles secured thereto and extending substantially normal therefrom.

5. The method of shaping the bristles of a toothbrush including a toothbrush head which includes a substantially flat elongate bristle support member comprising the steps of:

securing a ;plurality of elongate substantially straight bristles to opposite planar surfaces of the bristle support member of the toothbrush head, the bristles being arranged in tufted bundles, the bristle bundles secured to each surface being arranged in elongate rows extending longitudinally of the planar surface, the rows of bristle bundles including a plurality of interior rows, each of a pair of intermediate rows being positioned outwardly and adjacent separate ones of the outermost interior rows, and a pair of exterior rows, each exterior row being positioned adjacent to and outwardly of separate ones of said intermediate rows the bristles comprising the interior rows being of uniform length, the bristles of the intermediate rows being of uniform length, but having a length dimension greater than the length dimension of the bristles of the interior rows, the bristles comprising the exterior rows being of uniform length but having a length dimension greater than the length dimension of the bristles of the intermediate rows, positioning one of a pair of inverted channelshaped interior shaping members and one of a pair of intermediate shaping members in engaging relation with one planar surface of the bristle support member, each interior shaping member extending completely over the bristles comprising the interior rows, each intermediate shaping member interposed between said separating the bristles of the interior rows from the bristles of the intermediate rows, engaging the bristles of the exterior rows secured to one surface of the bristle support member with one pair of exterior shaping members and engaging the bristles of the exterior rows secured to the other surface of the bristle support member with a second pair of exterior shaping members to bend the bristles of each exterior row of one planar surface of the bristle support member towards the bristles of the other exterior row on said one planar surface, placing the toothbrush head and shaping members applied thereto in a heating chamber and heating the toothbrush head at a temperature within the range of 350 degrees to 380 degrees Fahrenheit for approximately 30 minutes, removing the toothbrush from the heating chamber and removing the shaping member from the toothbrush head.

* * * * *

UNITED STATES PATENT AND TRADEMARK OFFICE
CERTIFICATE OF CORRECTION

PATENT NO. : 5,027,463
DATED : July 2, 1991
INVENTOR(S) : Craig C. Daub

It is certified that error appears in the above-identified patent and that said Letters Patent is hereby corrected as shown below:

Column 9, line 34, delete ";plurality" and insert --plurality-- therefor.

Signed and Sealed this

Eleventh Day of August, 1992

Attest:

DOUGLAS B. COMER

*Attesting Officer*  *Acting Commissioner of Patents and Trademarks*